(12) United States Patent
Piskun

(10) Patent No.: US 8,439,831 B2
(45) Date of Patent: May 14, 2013

(54) LAPAROSCOPIC INSTRUMENT AND TROCAR SYSTEM AND RELATED SURGICAL METHOD

(75) Inventor: Gregory Piskun, Morganville, NJ (US)

(73) Assignee: Covidien LP, Mansfield, MA (US)

( * ) Notice: Subject to any disclaimer, the term of this patent is extended or adjusted under 35 U.S.C. 154(b) by 237 days.

(21) Appl. No.: 12/957,879

(22) Filed: Dec. 1, 2010

(65) Prior Publication Data

US 2012/0022334 A1 Jan. 26, 2012

Related U.S. Application Data

(63) Continuation of application No. 10/668,542, filed on Sep. 23, 2003, now Pat. No. 7,850,600.

(51) Int. Cl.
*A61B 1/32* (2006.01)

(52) U.S. Cl.
USPC ........... 600/208; 600/114; 600/206; 600/207; 606/205

(58) Field of Classification Search .......... 600/114–115, 600/201, 204, 207
See application file for complete search history.

(56) References Cited

U.S. PATENT DOCUMENTS

| | | |
|---|---|---|
| 2,669,991 A | 2/1954 | Curutchet |
| 4,016,884 A | 4/1977 | Kwan-Gett |
| 4,112,932 A | 9/1978 | Chiulli |
| 4,644,951 A | 2/1987 | Bays |
| 4,863,430 A | 9/1989 | Klyce et al. |
| 4,863,438 A | 9/1989 | Gauderer et al. |
| 5,026,366 A | 6/1991 | Leckrone |
| 5,159,921 A | 11/1992 | Hoover |
| 5,183,471 A | 2/1993 | Wilk |
| 5,241,968 A | 9/1993 | Slater |
| 5,242,409 A | 9/1993 | Buelna |
| 5,258,006 A | 11/1993 | Rydell et al. |
| 5,269,772 A | 12/1993 | Wilk |
| 5,312,391 A | 5/1994 | Wilk |
| 5,330,486 A | 7/1994 | Wilk |
| 5,334,143 A | 8/1994 | Carroll |
| 5,366,478 A | 11/1994 | Brinkerhoff et al. |
| 5,375,588 A | 12/1994 | Yoon |
| 5,383,852 A | 1/1995 | Stevens-Wright |
| 5,391,156 A | 2/1995 | Hildwein et al. |
| 5,395,327 A | 3/1995 | Lundquist et al. |
| 5,395,367 A | 3/1995 | Wilk |
| 5,441,483 A | 8/1995 | Avitall |

(Continued)

FOREIGN PATENT DOCUMENTS

| | | |
|---|---|---|
| EP | 0567146 | 10/1993 |
| EP | 0592244 | 4/1994 |

(Continued)

OTHER PUBLICATIONS

International Search Report for PCT/US05/24636 dated Jun. 20, 2006. (2 pages).
International Search Report of PCT/US08/03991 dated Jul. 30, 2008. (1 page).
European Search Report of EP 09252160 dated Mar. 17, 2010 (2 pages).
European Search Report for EP 09252168 dated Mar. 19, 2010 (3 pages).
International Preliminary Report on Patentability for PCT/US2008/003991 dated Oct. 6, 2009 (7 pages).
Notification of the Recording of a Change for PCT/US2008/003991 dated Mar. 23, 2010 (1 page).

(Continued)

*Primary Examiner* — Matthew J Kasztejna

(57) ABSTRACT

Laparoscopic instruments and cannulas are provided for performing laparoscopic procedures entirely through the umbilicus. Generally S-shaped laparoscopic instruments placed through the C-shaped trocar sleeves or through the cannula and instrument holder unit provide markedly improved degrees of instruments' freedom during trans-umbilical laparoscopic procedures.

7 Claims, 7 Drawing Sheets

U.S. PATENT DOCUMENTS

| | | | |
|---|---|---|---|
| 5,467,763 A | 11/1995 | McMahon et al. |
| 5,480,410 A | 1/1996 | Cuschieri et al. |
| 5,490,843 A | 2/1996 | Hildwein et al. |
| 5,522,791 A | 6/1996 | Leyva |
| 5,540,648 A | 7/1996 | Yoon |
| 5,545,179 A | 8/1996 | Williamson, IV |
| 5,549,563 A | 8/1996 | Kronner |
| 5,549,637 A | 8/1996 | Crainich |
| 5,571,115 A | 11/1996 | Nicholas |
| 5,571,137 A | 11/1996 | Marlow et al. |
| 5,575,799 A | 11/1996 | Bolanos et al. |
| 5,578,048 A | 11/1996 | Pasquallucci et al. |
| 5,603,723 A | 2/1997 | Aranyi et al. |
| 5,607,437 A | 3/1997 | Simon et al. |
| 5,634,911 A | 6/1997 | Hermann et al. |
| 5,634,937 A | 6/1997 | Mollenauer et al. |
| 5,651,771 A | 7/1997 | Tangherlini et al. |
| 5,653,705 A | 8/1997 | de la Torre et al. |
| 5,662,662 A | 9/1997 | Bishop et al. |
| 5,672,168 A | 9/1997 | de la Torre et al. |
| 5,683,378 A | 11/1997 | Christy |
| 5,725,536 A | 3/1998 | Oberlin et al. |
| 5,735,791 A | 4/1998 | Alexander, Jr. et al. |
| 5,782,859 A | 7/1998 | Nicholas et al. |
| 5,803,921 A | 9/1998 | Bonadio |
| 5,810,721 A * | 9/1998 | Mueller et al. ................ 600/206 |
| 5,830,191 A | 11/1998 | Hildwein et al. |
| 5,836,871 A | 11/1998 | Wallace et al. |
| 5,857,461 A | 1/1999 | Levitsky et al. |
| 5,860,995 A | 1/1999 | Berkelaar |
| 5,871,474 A | 2/1999 | Hermann et al. |
| 5,904,703 A | 5/1999 | Gilson |
| 5,906,577 A | 5/1999 | Beane et al. |
| 5,916,147 A | 6/1999 | Boury |
| 5,916,198 A | 6/1999 | Dillow |
| 5,931,832 A | 8/1999 | Jensen |
| 5,957,913 A | 9/1999 | de la Torre et al. |
| 5,964,781 A | 10/1999 | Mollenauer et al. |
| 5,997,515 A | 12/1999 | de la Torre et al. |
| 6,018,094 A | 1/2000 | Fox |
| 6,024,736 A | 2/2000 | de la Torre et al. |
| 6,033,378 A | 3/2000 | Lundquist et al. |
| 6,033,426 A | 3/2000 | Kaji |
| 6,042,573 A | 3/2000 | Lucey |
| 6,077,288 A | 6/2000 | Shimomura et al. |
| 6,086,603 A | 7/2000 | Termin et al. |
| 6,099,506 A | 8/2000 | Macoviak et al. |
| 6,142,936 A | 11/2000 | Beane et al. |
| 6,217,555 B1 | 4/2001 | Hart et al. |
| 6,217,590 B1 | 4/2001 | Levinson |
| 6,238,373 B1 | 5/2001 | de la Torre et al. |
| 6,264,604 B1 | 7/2001 | Kieturakis et al. |
| 6,315,770 B1 | 11/2001 | de la Torre et al. |
| 6,319,246 B1 | 11/2001 | de la Torre et al. |
| 6,440,061 B1 | 8/2002 | Wenner et al. |
| 6,440,063 B1 | 8/2002 | Beane et al. |
| 6,447,489 B1 | 9/2002 | Peterson |
| 6,454,783 B1 | 9/2002 | Piskun |
| 6,464,686 B1 | 10/2002 | O'Hara et al. |
| 6,468,292 B1 | 10/2002 | Mollenauer et al. |
| 6,488,620 B1 | 12/2002 | Segermark et al. |
| 6,488,692 B1 | 12/2002 | Spence |
| 6,537,209 B1 | 3/2003 | Pinkhasik et al. |
| 6,551,270 B1 | 4/2003 | Bimbo et al. |
| 6,558,371 B2 | 5/2003 | Dorn |
| 6,578,577 B2 | 6/2003 | Bonadio et al. |
| 6,582,364 B2 | 6/2003 | Butler et al. |
| 6,623,426 B2 | 9/2003 | Bonadio et al. |
| 6,669,674 B1 | 12/2003 | Macoviak et al. |
| 6,676,639 B1 | 1/2004 | Ternström |
| 6,706,050 B1 | 3/2004 | Giannadakis |
| 6,800,084 B2 | 10/2004 | Davison et al. |
| 6,811,532 B2 | 11/2004 | Ogura et al. |
| 6,846,287 B2 | 1/2005 | Bonadio et al. |
| 6,878,110 B2 | 4/2005 | Yang et al. |
| 6,890,295 B2 | 5/2005 | Michels et al. |
| 6,899,673 B2 | 5/2005 | Ogura et al. |
| 6,916,331 B2 | 7/2005 | Mollenauer et al. |
| 6,945,932 B1 | 9/2005 | Caldwell et al. |
| 6,972,026 B1 | 12/2005 | Caldwell et al. |
| 7,001,397 B2 | 2/2006 | Davison et al. |
| 7,008,377 B2 | 3/2006 | Beane et al. |
| 7,056,321 B2 | 6/2006 | Pagliuca et al. |
| 7,081,089 B2 | 7/2006 | Bonadio et al. |
| 7,195,590 B2 | 3/2007 | Butler et al. |
| 7,214,185 B1 | 5/2007 | Rosney et al. |
| 7,223,257 B2 | 5/2007 | Shubayev et al. |
| 7,223,278 B2 | 5/2007 | Davison et al. |
| 7,235,084 B2 | 6/2007 | Skakook et al. |
| 7,238,154 B2 | 7/2007 | Ewers et al. |
| 7,276,075 B1 | 10/2007 | Callas et al. |
| 7,300,399 B2 | 11/2007 | Bonadio et al. |
| 7,316,699 B2 | 1/2008 | McFarlane |
| 2002/0038077 A1 | 3/2002 | de la Torre et al. |
| 2002/0183594 A1 | 12/2002 | Beane et al. |
| 2003/0014076 A1 | 1/2003 | Mollenauer et al. |
| 2003/0036748 A1 | 2/2003 | Cooper et al. |
| 2003/0114832 A1 | 6/2003 | Kohler et al. |
| 2003/0135091 A1 | 7/2003 | Nakazawa |
| 2003/0208122 A1 | 11/2003 | Melkent |
| 2003/0236549 A1 | 12/2003 | Bonadio et al. |
| 2004/0049099 A1 | 3/2004 | Ewers et al. |
| 2004/0167543 A1 | 8/2004 | Mazzocchi et al. |
| 2005/0241647 A1 | 11/2005 | Nguyen et al. |
| 2005/0288558 A1 | 12/2005 | Ewers et al. |
| 2006/0020241 A1 | 1/2006 | Piskun et al. |
| 2006/0041188 A1 | 2/2006 | Dirusso et al. |
| 2006/0149306 A1 | 7/2006 | Hart et al. |
| 2006/0241651 A1 | 10/2006 | Wilk |
| 2006/0247498 A1 | 11/2006 | Bonadio et al. |
| 2007/0203398 A1 | 8/2007 | Bonadio et al. |
| 2007/0208312 A1 | 9/2007 | Norton et al. |
| 2007/0276430 A1 | 11/2007 | Lee et al. |
| 2008/0027476 A1 | 1/2008 | Piskun |
| 2008/0200767 A1 | 8/2008 | Ewers et al. |
| 2008/0255519 A1 | 10/2008 | Piskun et al. |
| 2009/0012477 A1 | 1/2009 | Norton et al. |

FOREIGN PATENT DOCUMENTS

| | | |
|---|---|---|
| EP | 1312318 | 5/2003 |
| EP | 1637086 | 3/2006 |
| EP | 1870043 | 12/2007 |
| EP | 2044889 | 4/2009 |
| WO | 93/14801 | 8/1993 |
| WO | 94/04067 | 3/1994 |
| WO | 97/42889 | 11/1997 |
| WO | 99/16368 | 4/1999 |
| WO | 02/07611 | 1/2002 |
| WO | 2006/019723 | 2/2006 |
| WO | 2006/100658 | 9/2006 |
| WO | 2006/113216 | 10/2006 |
| WO | 2008/015566 | 2/2008 |
| WO | 2008/121294 | 10/2008 |

OTHER PUBLICATIONS

Written opinion of the International Searching Authority for PCT/US2008/03991 dated Jul. 30, 2008 (6 pages).

International Preliminary Report on Patentability for PCT/US2005/024636 dated Jan. 23, 2007. (1 page).

Written Opinion of the International Searching Authority for PCT/US2005/024636 dated Sep. 5, 2006 (5 pages).

International Search Report for PCT/US05/24636 dated Sep. 5, 2006 (3 pages).

International Search Report for PCT/US05/24111 dated Aug. 24, 2006 (2 pages).

Written Opinion of the International Searching Authority for PCT/US2005/024111 dated Aug. 24, 2006. (3 pages).

International Preliminary Report on Patentability for PCT/US2005/024111 dated Jan. 23, 2007 (4 pages).

* cited by examiner

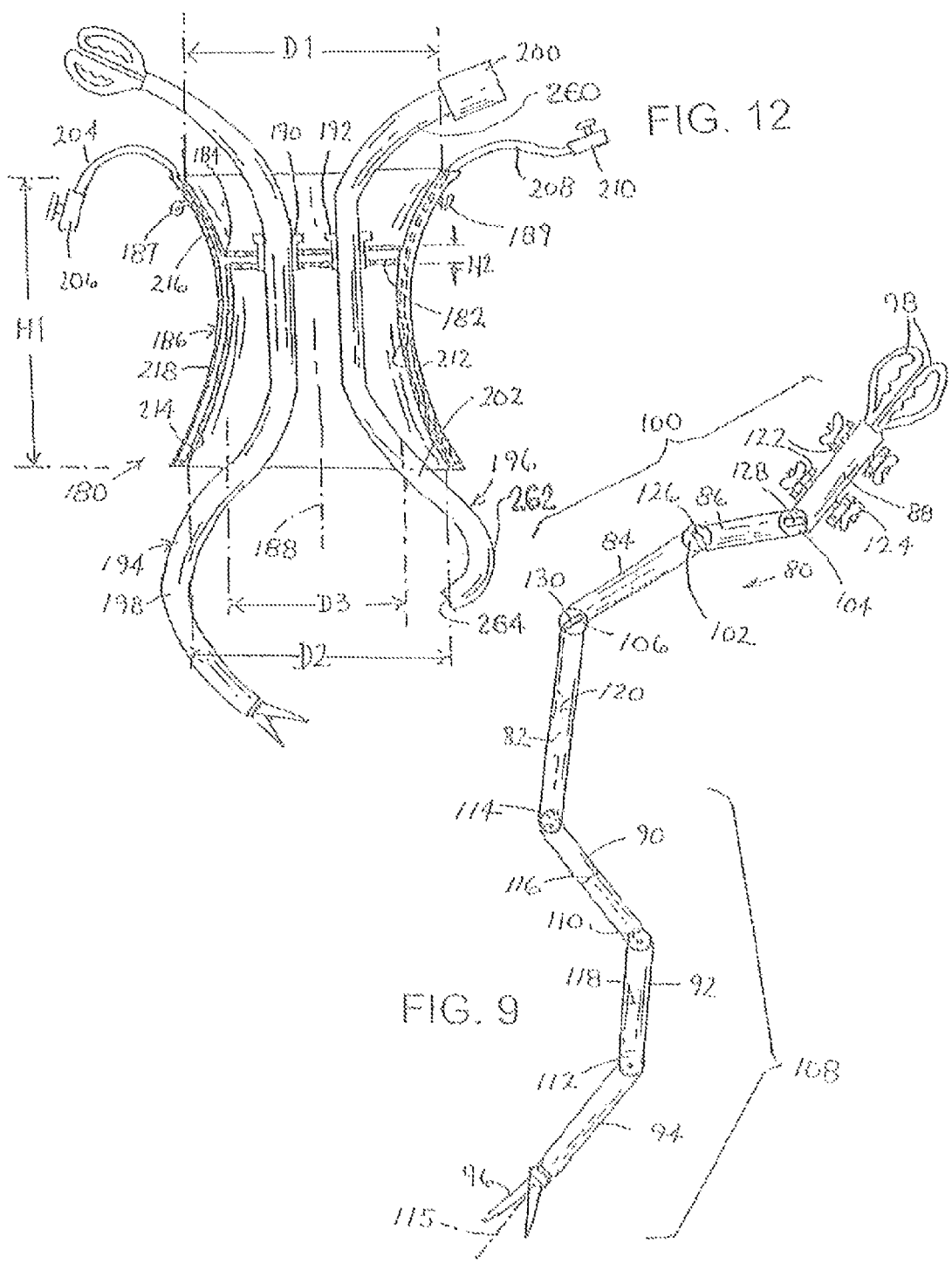

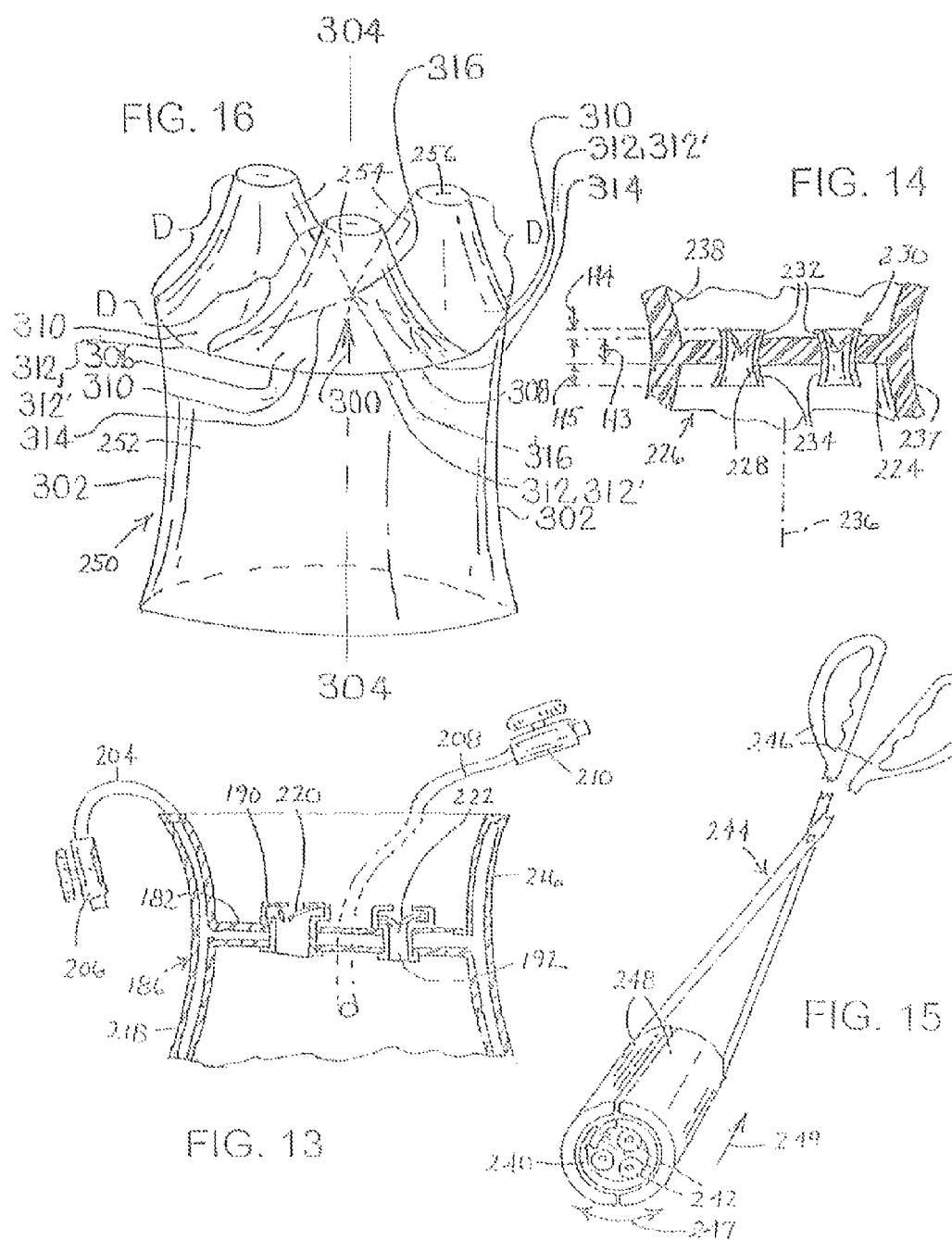

LAPAROSCOPIC INSTRUMENT AND TROCAR SYSTEM AND RELATED SURGICAL METHOD

CROSS-REFERENCE TO RELATED APPLICATIONS

This application is a continuation of U.S. patent application Ser. No. 10/668,542 filed on Sep. 23, 2003 by Piskun, entitled "LAPAROSCOPIC INSTRUMENT AND TROCAR SYSTEM AND RELATED SURGICAL METHOD", now U.S. Pat. No. 7,850,600 issued on Dec. 14, 2010, the entire contents of which is incorporated by reference herein.

FIELD OF INVENTION

The present invention relates to the surgical instruments, and particularly to laparoscopic instruments, which facilitate the performance of laparoscopic procedures entirely through the umbilicus.

BACKGROUND

Abdominal laparoscopic surgery gained popularity in the late 1980's, when benefits of laparoscopic removal of the gallbladder over traditional (open) operation became evident. Reduced postoperative recovery time, markedly decreased post-operative pain and wound infection, and improved cosmetic outcome are well established benefits of laparoscopic surgery to perform an operation utilizing smaller incisions of the body cavity wall.

Laparoscopic procedures generally involve insufflation of the abdominal cavity with $CO_2$ gas to a pressure of around 15 mm Hg. The abdominal wall is pierced and a 5-10 mm in diameter straight tubular cannula or trocar sleeve is then inserted into the abdominal cavity. A laparoscopic telescope connected to an operating room monitor is used to visualize the operative field, and is placed through (one of) the trocar sleeve(s). Laparoscopic instruments (graspers, dissectors, scissors, refractors, etc.) are placed through two or more additional trocar sleeves for the manipulations by the surgeon and surgical assistant(s).

Recently, so called "mini-laparoscopy" has been introduced utilizing 2-3 mm diameter straight trocar sleeves and laparoscopic instruments. When successful, mini-laparoscopy allows further reduction of abdominal wall trauma and improved cosmesis. However, instruments used for mini-laparoscopic procedures are generally more expensive and fragile. Because of their performance limitations, due to their smaller diameter (weak suction-irrigation system, poor durability, decreased video quality), mini-laparoscopic instruments can generally be used only on selected patients with favorable anatomy (thin cavity wall, few adhesions, minimal inflammation, etc.). These patients represent a small percentage of patients requiring laparoscopic procedures. In addition, smaller, 2-3 mm, incisions may still cause undesirable cosmetic outcomes and wound complications (bleeding, infection, pain, keloid formation, etc.).

Since the benefits of smaller and fewer body cavity incisions are proven, it would be attractive to perform an operation utilizing only a single incision in the navel. An umbilicus is the thinnest and least vascularized, and a well-hidden, area of the abdominal wall. The umbilicus is generally a preferred choice of abdominal cavity entry in laparoscopic procedures. An umbilical incision can be easily enlarged (in order to eviscerate a larger specimen) without significantly compromising cosmesis and without increasing the chances of wound complications. The placement of two or more standard (straight) cannulas and laparoscopic instruments in the umbilicus, next to each other, creates a so-called "chopstick" effect, which describes interference between the surgeon's hands, between the surgeon's hands and the instruments, and between the instruments. This interference greatly reduces the surgeon's ability to perform a described procedure.

Thus, there is a need for instruments and trocar systems which allow laparoscopic procedures to be performed entirely through the umbilicus, while at the same time reducing or eliminating the "chopstick effect". A laparoscopic procedure performed entirely through the umbilicus, using the laparoscopic instruments and trocar system according to an embodiment of the present invention, allows one to accomplish the necessary diagnostic and therapeutic tasks while further minimizing abdominal wall trauma and improving cosmesis.

SUMMARY OF THE INVENTION

A general object of the present invention is to provide a laparoscopic instrument and an instrument or cannula holder for use in the performance of laparoscopic procedures, for instance, entirely through the umbilicus.

A more specific object of the present invention is to provide a laparoscopic instrument, which may markedly increase the workspace between the laparoscopic instruments and between the hands of the surgeon where more than one instrument shaft is inserted through the same opening in the patient's abdominal wall.

A more general object of the present invention is to provide a laparoscopic instrument that has enhanced operational flexibility to facilitate the performance of laparoscopic surgical procedures.

A related object of the present invention is to provide a cannula or instrument holder utilizable in combination with such a laparoscopic instrument to facilitate the performance of a laparoscopic procedure through a single opening in the patient's abdominal wall, for instance, in the patient's umbilicus.

Another object of the present invention is to provide generally S-shaped laparoscopic instruments.

In one embodiment of the present invention, a stand-alone laparoscopic medical instrument insertable through a laparoscopic trocar sleeve comprises an elongate shaft, an operative tip disposed at one end of the shall, and an actuator disposed at an opposite end of the shaft, the actuator being operatively connected to the operative tip via the shaft for controlling the operation of the operative tip. The shaft has a proximal end portion and middle portion and a distal end portion, at least the distal end portion being independently bendable to form a C shape. The distal segments of the shall are rotatable about a longitudinal axis at least one location along the instrument's shall, preferably at the operative tip or proximal to the operative tip.

Pursuant to additional features of the present invention, the distal end portion of the instrument shall is continuously bendable into a smoothly curved C-shaped configuration, while a lock is operatively connected to the shaft for releasably maintaining the C-shaped curved configuration. Moreover, the distal end portion may be provided with an articulated joint, whereby the distal end portion is swingable relative to the middle portion of the shaft. The proximal end portion may also be independently bendable to form a C shape.

In a further embodiment of the present invention, a stand-alone laparoscopic medical instrument insertable through a laparoscopic trocar sleeve comprises an elongate shaft, an operative tip disposed at the one end of the shall, and an actuator disposed at an opposite end of the shaft. The actuator is operatively connected to the operative tip via the shaft for controlling the operation of the operative tip. The shaft has a proximal end portion and a distal end portion, the distal end portion being continuously bendable to form a smoothly curved C shape. The distal end portion is connected to the proximal end portion via an articulated joint, whereby the distal end portion may be laterally swung with the reference to the proximal end portion.

In this further embodiment of the invention, the proximal end portion of the instrument shaft may include a rigid segment connected to the distal end portion via the articulated joint. The proximal end portion may additionally include a flexible segment connected to the rigid segment on a side thereof opposite the distal end portion, the actuator being connected to a free end of the flexible segment, opposite the rigid segment.

A stand-alone laparoscopic medical instrument insertable through a laparoscopic trocar sleeve comprises, in accordance with another embodiment of the present invention, an elongate shaft, an operative tip disposed at one end of shall, and a manual actuator disposed at an opposite end of the shaft, the manual actuator being operatively coupled to the operative tip via the shaft. A first mechanism is operatively connected to the shall for bending a proximal portion of the shaft in a first direction, while a second mechanism is operatively connected to the shall for bending a distal portion of the shaft in a second direction different from the first direction, whereby the shall assumes a shape with a plurality of differently shaped segments.

The shaft has a longitudinal axis at the one end, and the instrument further comprises a rotation mechanism operatively connected to the shall for rotating the operative tip about the axis.

Pursuant to another feature of this other embodiment of the invention, first locking element is operatively connected to the first mechanism and a second locking element is operatively connected to the second mechanism, whereby the proximal portion and the distal portion may be maintained as the differently shaped segments. Where the proximal portion and the distal portion are bendable by the first mechanism and the second mechanism in a common plane, the instrument may further comprise an additional mechanism operatively connected to the shaft for bending the distal portion of the shall in an additional direction out of the plane.

Where the proximal portion of the shall assumes a first C-shaped configuration in response to the operation of the first mechanism and the distal portion of the shaft assumes a second C-shaped configuration in response to operation of the second mechanism, the C-shaped configurations may face opposite sides of the shaft.

A laparoscopic medical instrument comprises, in accordance with an additional embodiment of the present invention, an elongate flexible shall, an operative tip disposed at one end of the shall, and a manual actuator disposed at an opposite end of the shaft, the manual actuator being operatively coupled to the operative tip via the shaft, a first bending mechanism being operatively connected to the shall for curving a proximal portion of the shaft in a first direction, and a second bending mechanism being operatively connected to the shaft for curving a distal portion of the shaft in a second direction different from the first direction, whereby the shaft assumes a shape with a plurality of arcuate segments.

The instrument of this additional embodiment of the invention may additionally comprise a rotation mechanism operatively connected to the shall for rotating the operative tip about the axis, a first locking element operatively connected to the first bending mechanism and a second locking element operatively connected to the second bending mechanism. The bending mechanisms each include a manual actuator mounted to the shaft at the other end thereof.

A holder for cannulas and instruments in laparoscopic surgical operations comprises, in accordance with the present invention, a plate member having a surrounding edge and a wall surrounding the plate member, the wall being connected to the plate member all along the edge. The wall has a longitudinal axis, while the plate member extends substantially transversely to the axis. The plate member may be provided with a plurality of apertures for receiving respective elongate laparoscopic surgical members.

The height dimension of the wall of the cannula and instrument holder is at least as great as, and preferably substantially greater than, the height dimension of the plate member. The wall may have at least one end portion extending as a flange to the plate member. In at least one embodiment of the cannula and instrument holder, the wall has two end portions extending as endless flanges to the plate, with the plate member being located at one end of the wall and with the plate member and the wall forming a cup shape.

The inner diameter of the wall of the cannula and instrument holder at an end opposite the plate member is preferably larger than the inner diameter of the wall at the plate member, so that the cannula and instrument holder has a flared or tapered profile.

Pursuant to further features of the present invention, the plate member and/or the wall of the cannula and instrument holder is inflatable, while the plate member is provided at the apertures with extensions elongating the apertures. The height of the plate member, in a direction parallel to the axis of the cannula and instrument holder, is at least as great as the height of the extensions. Preferably, the plate member is flexible.

Pursuant to another feature if the present invention, where the apertures in the plate member of the cannula and instrument holder have a longitudinal dimension extending generally parallel to the axis, at least one of the apertures has a curvilinear or arced shape along the longitudinal dimension of the one or the apertures.

The wall of the cannula and instrument holder may be flexible and at least partially curved in a direction parallel to the axis oldie holder.

At least one of the plate member and the wall of the cannula and instrument holder is provided with a gas channel for the introduction of an insufflation gas into a patient. In addition, the wall is advantageously provided with an anchoring element for securing the holder to a patient. The anchoring element is preferably taken from the group consisting of a hook and an eyelet.

BRIEF DESCRIPTION OF THE DRAWINGS

FIG. 9 is a schematic side elevational view of a laparoscopic instrument in accordance with the present invention.

FIG. 12 is a schematic cross-sectional view of a laparoscopic instrument or cannula holder in accordance with the present invention.

FIG. 13 is a partial view similar to FIG. 12 of the laparoscopic instrument or cannula holder of that drawing figure.

FIG. 14 is a partial cross-sectional view of another laparoscopic instrument or cannula holder in accordance with the present invention.

FIG. 15 is a schematic perspective view of a laparoscopic instrument or cannula holder in a collapsed configuration between jaws of a deployment instrument.

FIG. 16 is a schematic perspective view of another laparoscopic instrument or cannula holder in accordance with the invention.

DETAILED DESCRIPTION

Figure 1:
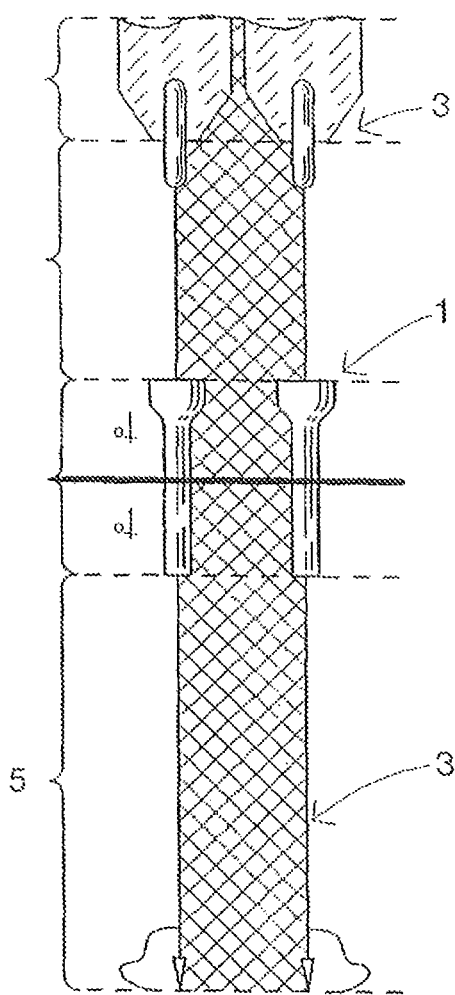
FIG. 1 is a schematic view of a conventional laparoscopic instrument inserted through a conventional straight trocar sleeve or cannula.

The present invention provides laparoscopic instruments and trocar sleeves or cannulas for the performance of laparoscopic procedures entirely through the umbilicus. The instruments may, however, be used to perform laparoscopic procedures at locations on a patient other than the umbilicus. Referring now in specific detail to the drawings, in which like reference numerals identify similar or identical elements, there is shown in FIG. 1 a conventional, prior art laparoscopic instrument-trocar assembly.

As illustrated in FIG. 1, a conventional trocar sleeve or cannula 1 is an essentially straight, hollow instrument, which allows conventional laparoscopic instruments 3 such as an endoscope of suitable diameter to be inserted through the conventional cannula 1 and into the abdominal cavity 5 of a patient. Conventional cannulas 1 have a diameter of around 2-15 mm. Once the conventional laparoscopic instruments 3 are in place, standard laparoscopic procedures may be performed, such as cholecystectomy, appendectomy, or simple diagnostic laparoscopy.

As shown in FIG. 1, when conventional trocar sleeves or cannulas 1 and conventional laparoscopic instruments 3 are inserted only through the umbilicus of the patient, the close proximity of the instruments to each other results in the so-called chopstick effect, which is a significant limitation to the manipulation of conventional laparoscopic instruments 3 through conventional trocars 1.

Figure 2A:
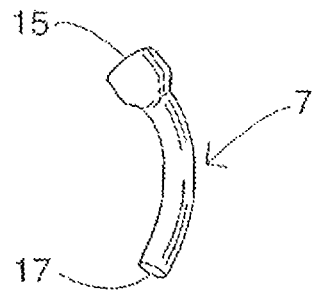
FIG. 2A is a side view and FIG. 2B is an end view of an exemplary embodiment of a flexible C-shaped trocar sleeve or cannula.
Figure 2B:

As shown in FIG. 2A and FIG. 2B, an exemplary C-shaped trocar sleeve or cannula 7 is generally an elongated tube having a proximal end 15 and a distal end 17. In one exemplary embodiment the C-shape curve through ends 15, 17 is bent so that each end portion forms an angle of approximately 30° with respect to a tangent to the center of the trocar sleeve or cannula 7. However, any angle, which sufficiently reduces the chopstick effect, may be used. Thus, exemplary embodiments with angles from 5-45° may be used. A C-shaped trocar sleeve or cannula 7 may be made of conventional material as is known in the art. The interior diameter of a C-shaped cannula 7 is preferably around 5 mm. However, in alternate embodiments the interior diameter of the C-shaped cannula 7 may range from 2-15 mm. In one exemplary embodiment, the C-shape is relatively fixed and does not vary, for example when the cannula 7 has a rigid composition. In an alternate exemplary embodiment, the C-shaped cannula 7 is more flexible allowing the surgeon or surgical assistant to bend the cannula 7 changing the angle of the C-shape, for example, via insertion of an instrument into the cannula.

In an alternative design, trocar sleeve or cannula 7 is made of a flexible material with a memory. Trocar sleeve 7 or cannula 7 may have a straight or linear cylindrical configuration in relaxed state, i.e., in the absence of externally applied forces. Sleeve or cannula 7 assumes the curved or arcuate configuration shown in FIG. 2A upon the insertion through the cannula of a laparoscopic instrument shaft with a curved or arcuate section of sufficiently greater rigidity than the cannula. Cannula 7 then bends through the application of external forces to take the arcuate form shown in FIG. 2A.

Figure 2C:
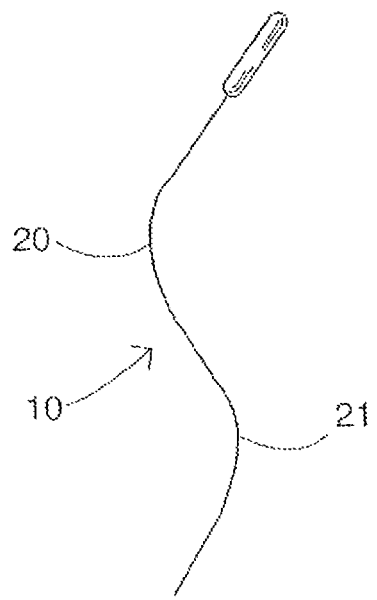
FIG. 2C is an exemplary embodiment of an S-shaped instrument.

FIG. 2C illustrates an exemplary S-shaped laparoscopic instrument 10. The S-shaped laparoscopic instrument 10, has for example, a shaft 10a with a preformed inherently S-shaped configuration including a proximal curve 20 and a distal curve 21. Examples of laparoscopic instruments 10 which can be formed generally into an S-shape include but are not limited to scissors, clamps, dissectors, staplers, clip appliers, retrieval bags, and electrocautery instruments. Instruments 10 include a manual actuator 10b at a proximal end and an operative tip 10c at a distal end. The S-shaped shaft 10a may be substantially rigid throughout. Alternatively, shaft 10a or a portion thereof, for example, distal curve 21, may be semi-rigid and flexible so that the shaft may be deformed from the S-shaped configuration to an at least partially straightened configuration upon application of deformation forces to the shaft. In the latter case, the shaft is made of a material with a memory so that the shaft automatically returns to the S-shaped configuration after relaxation of deformation forces. In another alternative, proximal shaft portion 20 is rigid while distal shaft portion 21 is flexible. Distal portion 21 is flexed into substantially rigid C-shape by a locking mechanism (not separately shown), controlled by actuator 10b, so the instrument assumes a rigid S-form when needed by the surgeon. In any event, the S-shape for these instruments can be achieved, for example, by using conventional manufacturing techniques modified to accommodate the S-shape contour of the instrument.

Figure 3:
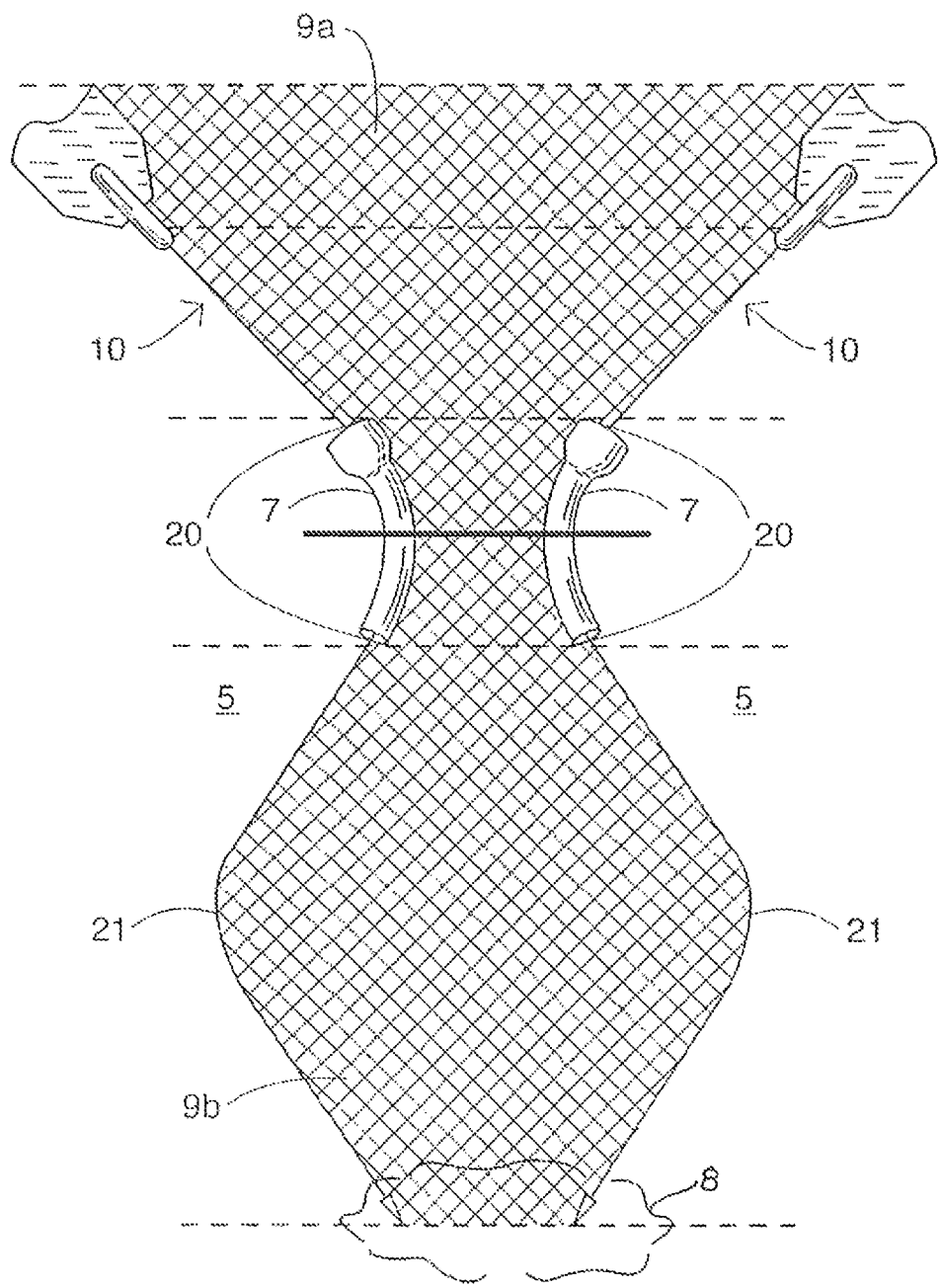
FIG. 3 is a schematic view of an exemplary embodiment of an S-shaped laparoscopic instrument inserted through a C-shaped flexible trocar sleeve or cannula.

As illustrated in FIG. 3, a generally S-shaped laparoscopic instrument 10 may be inserted through a C-shaped trocar sleeve or cannula 7. For example, the proximal curve 20 of the S-shaped instrument 10 corresponds to the curve of the C-shaped cannula 7. The distal curve 21 of the S-shaped instrument 10 also corresponds to the curve of the C-shaped cannula 7 and when inserted through the C-shaped cannula 7 will be, for example, entirely within the abdominal cavity 5 of the patient. A C-shaped cannula 7 and S-shaped laparoscopic instrument 10 allows the surgeon to perform the laparoscopic procedure without making incisions outside of the umbilicus. In accordance with the present invention, the size and curvature of a C-shaped cannula 7 will correspond to the size and curvature of an S-shaped instrument 10 and can include any desired size.

This arrangement of C-shaped cannula 7 and S-shaped instrument 10 eliminates the "chopstick effect" which results from the insertion of conventional laparoscopic instruments 3 through the umbilicus. For example, the proximal curves of the S-shaped instruments 10 and the C-shaped cannula 7 allows the surgeon's hands and the proximal portions of the instruments 20, including the instruments' handles, to be placed as far apart as is convenient for the surgeon. For example, workspace 9a is created. Movement of the proximal portion of one instrument 20 away from the proximal portion 20 of the other also markedly separates the exposed (e.g. outside the body cavity) shafts of each instrument. The distal curve of the S-shaped instrument 21 creates workspace 9b between the portions of the instruments in the abdominal cavity and redirects the distal end of the laparoscopic instrument 10 back toward a target site 8, such as an abdominal organ or other abdominal structure or site.

Thus, an S-shaped laparoscopic instrument 10 may be though of as having four segments or sections to allow an abdominal procedure to be performed entirely through the umbilicus and yet overcome the "chopstick effect" encountered with conventional laparoscopic instruments 3 and cannulas 1. First, the portion outside of the patient's abdominal cavity 5 allows sufficient space between the surgeon's hands when manipulating the proximal portion of the laparoscopic instruments 10. Second, the portion at or near the umbilicus, which allows a laparoscopic instrument 10 to enter the abdominal cavity 5 is in close proximity to one or more additional laparoscopic instruments 10 so that all instruments 10 enter the abdomen through the umbilicus. Third, the portion beyond the second portion, which creates separation between laparoscopic instruments 10 within the abdominal cavity 5. Fourth, the distal end of a laparoscopic instrument 10 is shaped to point hack toward the target abdominal organ, tissue or other site.

Examples of procedures which can be facilitated by the use of C-shaped trocar sleeves or cannulas 7 and S-shaped laparoscopic instruments 10 include, but are not limited to diagnostic laparoscopy, cholecystectomy, appendectomy, salpingectomy, oophorectomy, treatment of infertility and extrauterine pregnancy, hysterectomy, removal of a section of bowel, a variety of gastric procedures, biopsy of various abdominal organs, including liver, and hernia repair.

The following discussion describes, as an example, a cholecystectomy procedure as described in FIGS. 2A-C and FIG. 3. It should be noted, however, that many other laparoscopic procedures may be performed using various embodiments disclosed herein. The following description, therefore, is merely illustrative and is not intended to limit the present invention to the description given in this example.

A laparoscopic procedure, such as a cholecystectomy, using a curved C-shaped flexible or rigid trocar sleeve or cannula 7 and S-shaped laparoscopic instruments 10 is performed with the patient under general anesthesia. Carbon dioxide gas is insufflated intra-abdominally to 15 mm Hg through a 5 mm lateral umbilical incision, using for example, a VERESS™ needle. For example, two curved C-shaped 5 mm cannulas 7 are then inserted through an incision in the umbilicus. The surgeon operates, for example, a 5 mm endoscope with one hand and a 5 mm S-shaped laparoscopic instrument 10 with the other, each of which is passed through a respective cannula 7.

The cannula for the endoscope could be straight so that a conventional straight endoscope could be used, the other curved cannula 7 providing separation between the instruments and the surgeon's hands. Pericholecystic adhesions, if present, are removed by blunt or sharp dissection using an S-shaped dissector to expose the dome of the gallbladder. A 2-0 nylon (or other suitable material) stay suture on a needle is placed through the abdominal wall immediately below the right costal margin at the right anterior axillary line, allowing for superior retraction of the gall bladder dome. The removal of the adhesions from around the gallbladder infundibulum is then continued as necessary. A second stay suture is placed through the right flank and then through the neck of the gallbladder allowing for lateral retraction to expose the cystic structures. The cystic duct and cystic artery are dissected, then ligated with clips, utilizing a 5 mm S-shaped clip applier, and then finally transected with an S-shaped scissors. With continued retraction from stay sutures, the gallbladder is removed from the liver bed utilizing an S-shaped electrocautery device equipped with a hook, dissecting the gallbladder from medial to lateral and inferior to superior direction. The perihepatic area is then irrigated using an S-shaped irrigation/suction device.

The above-described procedure is greatly facilitated by the use of S-shaped laparoscopic instruments 10 and C-shaped cannulas 7, allowing the procedure to be performed entirely through the umbilicus while at the same time reducing or eliminating the "chopstick effect". For example, each of the S-shaped laparoscopic instruments is inserted and removed from the active curved cannula 7 as needed during the procedure and conflict with the endoscope is avoided. Thus, as a result, improved cosmesis, reduced operative and post-operative complications, and a less complicated surgical technique are achieved.

Figure 4A:
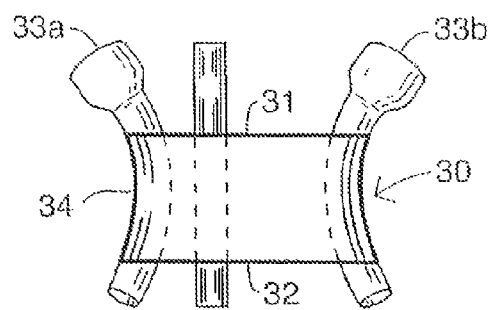
FIG. 4A is a lateral view and FIG. 4B is a perspective view of an exemplary inflatable unit with multiple C-shaped trocar sleeve or cannulas incorporated within the unit.
Figure 4B:
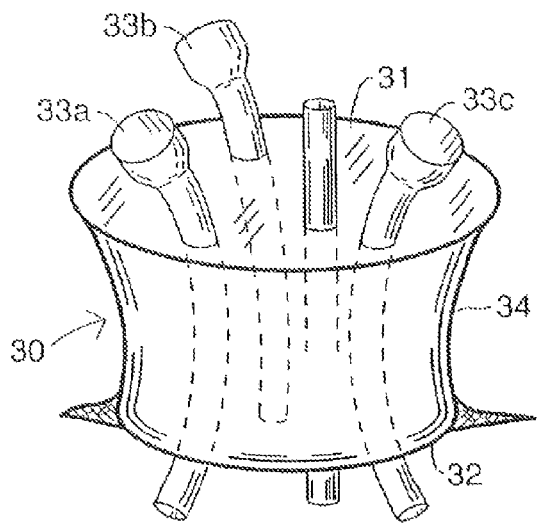

FIG. 4A and FIG. 4B illustrate an inflatable cannula holder 30 having, for example, multiple C-shaped trocar sleeves or cannulas incorporated within the unit 30. The lateral wall 34 oldie inflatable cannula holder unit 30 may vary from extremely flexible and stretchable when deflated, thus facilitating insertion into the umbilical incision, to somewhat rigid when inflated during the surgical procedure. The inflatable unit 30 has, for example, a horizontal upper plate 31 and a horizontal lower plate 32. Curved or arcuate trocar sleeves or cannulas 33a, 33b, and 33c will extend through separate and mutually spaced apertures (not designated) in the horizontal upper plate 31 and separate and mutually spaced apertures (not designated) in the horizontal lower plate 32 and may be incorporated within the lateral wall 34. Cannulas 33a, 33b, 33c may be rigid or flexible members. One or more straight trocar sleeves or cannulas 33d may also be provided which traverse holder unit 30 and particularly upper surface 31 and lower surface 32 thereof. Any given straight cannula 33d may be rigid or flexible. In the latter case, the cannula 33d may be sufficiently flexible to bend in conformation to a generally C-shaped section 20 or 21 (FIG. 2C) of laparoscopic instrument 10. Shaft 10a or section 20, 21 thereof is either rigid or has a sufficiently rigidity to force the bending of cannula 33d. One or more of cannulas 33a, 33b and 33c may similarly be flexible members with a memory tending to return the cannulas to a straight or arcuate configuration.

Rigid sections may be inserted or attached around the periphery of the horizontal upper 31 or lower 32 plate to add stability. The horizontal upper plate 31 and horizontal lower plate 32 may be, for example concave or straight. At least one and possibly two or more C-shaped trocar sleeves or cannulas 33a, 33b, 33c, (described previously) can be incorporated within the lateral wall 34 of the inflatable unit 30 and are distributed, for example, evenly around the wall 34 of the unit 30. The upper 31 and lower plate 32 are preferably made of a flexible plastic material or other suitable surgical quality material.

In an alternate embodiment, the inflatable unit 30 has one or more C-shaped trocar sleeves or cannulas 7 incorporated within its lateral wall 34, and one or more straight cannula 1, also incorporated within the inflatable unit's lateral wall 34. The straight cannula may accommodate, for example, a straight endoscopic or laparoscopic instrument, while the C-shaped cannulas 7 can accommodate an S-shaped instrument 10 as described above. Thus, even where one of the instruments is relatively straight and passes through a relatively straight cannula 1, the chopstick effect is still reduced as a result of the remaining C-shaped cannulas 7 and S-shaped instruments 10, which provide space between the surgeons hands, the proximal portions of laparoscopic instruments (which includes the straight laparoscope), and the distal ends of the laparoscopic instruments (which also include the straight laparoscope).

Inflatable unit 30 may include one or more passageways 40a and 40d formed by generally cylindrical webs of resilient material (not separately designated) connected at opposite ends to upper surface 31 and lower surface 32. Upon inflation of unit 30, the webs close the passageways and, upon insertion of respective cannulas 33a and 33d, form a sealed engagement therewith. In one possible mode of use, cannulas 33a and 33d are inserted through passageways 40a and 40d only after placement of unit 30 in an opening formed in a patient and upon inflation of the unit. Alternatively, all cannulas 33a, 33b, 33c, 33d may be disposed within and coupled to unit 30 prior to the positioning thereof in the patient.

The surgeon may place the inflatable unit 30 through an approximately 1.51 to 2.5 cm incision in the umbilicus. The unit 30 is inserted prior to inflation with the C-shaped cannulas 33a, 33b, 33c, for example, parallel and in close proximity to each other. The upper plate 31 will remain outside of the umbilicus while the lower plate 32 is located just inside the abdominal cavity 5. Once the unit 30 is properly positioned, the surgeon or assistant may inflate the unit 30. The unit 30 may be inflated via, for example, a one-directional valve using a syringe or gas line inserted into a narrow hollow tube connected to the unit 30 as is known in the art. The syringe or gas line may be alternatively inserted directly into a one-directional valve. Thus, means for inflating the unit 30 can similar to the means for inflating a conventional endotracheal tube.

In an exemplary embodiment, the diameter of the inflatable unit 30 increases upon inflation. The unit may be inflated to the extent needed for the particular laparoscopic procedure. By placing the trocar sleeves or cannulas in the lateral walls of the inflatable unit, the surgeon may position a trocar sleeves or cannulas, and thus an instrument inserted through a cannula, as far away from the other cannulas and instruments as possible within the confines of a chosen space such as the umbilicus. In addition, the surgeon may change the position of the cannulas and instruments within the umbilicus by rotating the inflatable unit 30 around its vertical axis. Moreover, the inflatable unit 30 seals the opening of the patient's abdominal cavity 5 to prevent leakage of $CO_2$ from the abdominal cavity.

Figure 8:
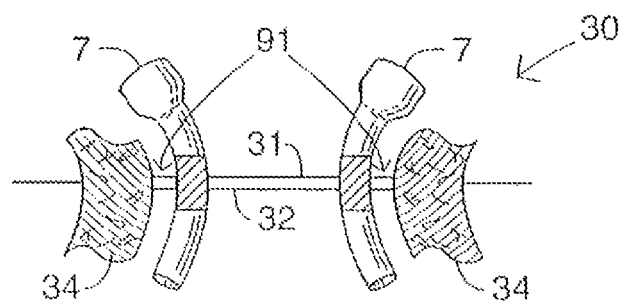
FIG. 8 is a cross-sectional view of an exemplary embodiment of an inflatable unit having multiple cannulas incorporated within the unit.

In an alternate embodiment as shown in FIG. 8, the distance between the upper plate 31 and the lower plate 32 may be reduced, thereby increasing the ability of the trocar sleeve or cannula 7 to move in relation to the wall of the inflatable unit 30. This design, where the distance between 31 and 32 is reduced to form the "plate member," is preferred. The plate member is located perpendicular to the axis of the cannula holder and anywhere within its walls.

Thus, as an example, the cholecystectomy procedure described above may be performed using the inflatable unit 30 in conjunction with S-shaped laparoscopic instruments 10, rather than using separate cannula/instrument arrangements. Once the gallbladder is transected and removed from the liver bed, it is removed through the 1.5 to 2.5 mm incision along with the inflatable unit 30. If necessary, the initial incision can be extended to remove the gallbladder. Alternatively, the gallbladder may be opened to remove or crush and remove gallstones, facilitating removal of the gallbladder through the umbilical incision.

Figure 5A:
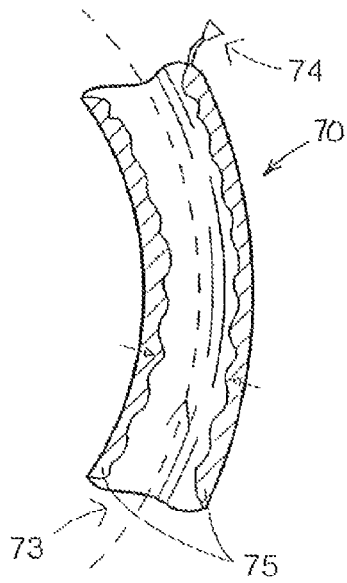
FIG. 5A is a non-inflated lateral view and FIG. 5B is an inflated lateral view of an exemplary inflatable C-shaped trocar sleeve or cannula having a balloon-like structure within the hollow body of the cannula.
Figure 5B:
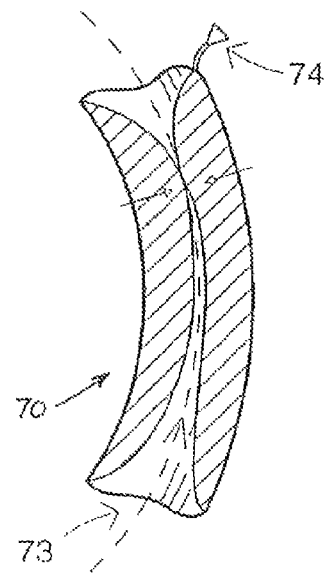

As shown in FIG. 5A and FIG. 5B, an inflatable unit 70 includes a single C-shaped trocar sleeve or cannula (not separately designated) having a radially expandable and inflatable balloon-like structure 75 incorporated within the hollow lumen 73 of the cannula. A single laparoscopic instrument may be inserted within this inflatable unit 70.

Unit 70 may then be inflated to secure the cannula and laparoscopic instrument together as one movable unit. The inflatable unit 70 may be inflated via, for example, a one-directional valve using a syringe or gas line inserted into a narrow hollow tube 74 connected to the unit 70 as is known in the art. The syringe or gas line may be alternatively inserted directly into a one-directional valve. Thus, means for inflating the unit 70 can be similar to the means for inflating a conventional endotracheal tube. Inflating the inflatable unit 70 also serves to seal the abdomen preventing insufflated gas from escaping through the lumen of the cannula. The inflatable unit 70 may then be deflated, the laparoscopic instrument may be removed, and a different instrument may be inserted.

While the above description of S-shaped instruments 10 and C-shaped cannulas 7 has been directed to procedures performed entirely through the umbilicus, it is to be understood that embodiments of the present invention may be adapted for use in other entry sites. Therefore, when it is desirable to have entry of multiple instruments in a relatively localized area, embodiments of the present invention may be used for such entry; while reducing or eliminating the so-called "chopstick effect". Thus, existing scars or hidden areas such as the pubic hair line or the axillary region may be used as a localized entry site.

Figure 6:
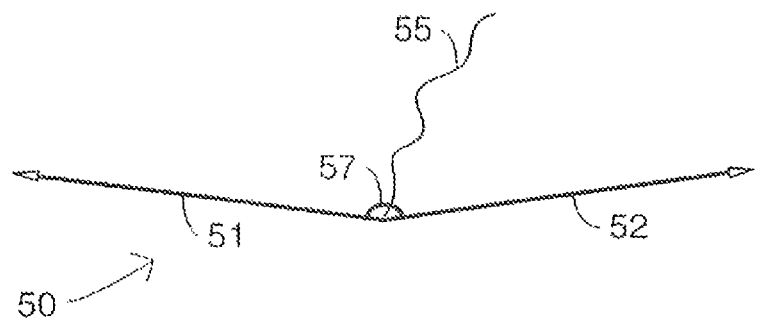
FIG. 6 is a lateral view of an exemplary angulated needle with two sharp ends and a thread attached at the angle of the needle.

As illustrated in FIG. 6, an angulated bi-directional needle 50 is provided with a first sharp end 51, a second sharp end 52, and a surgical thread 55 attached to the angle 57 of the needle 50. The needle 50 has, for example, a total length of around 5-10 cm. The length of each segment from the angle to sharp end is roughly equivalent, but need not be. An acute angle of around 160° is formed by the angulated needle 50, however angles 57 ranging from a straight needle, i.e. 180°, to an acute angle 57 of around 90° may be used. The needle is formed out of steel or other suitable material. The surgical thread 55, such as 2-0 nylon, is attached at the angle 57 of the needle 50.

The angulated needle 50 simplifies suture delivery through the gallbladder or other abdominal structure. For example, the first sharp end 51 of the needle 50 is inserted through the body wall by the surgeon. The needle 50 is then grasped within the abdominal cavity 5 by a laparoscopic instrument under endoscopic guidance and is pulled toward the organ of interest. With the second sharp end 52 leading, a stitch is placed through the abdominal structure of interest. The second sharp end 52 is then delivered through the abdominal wall.

The angulated bi-directional needle 50 allows delivery of a switch without changing the orientation of the sharp end as would be necessary if a needle with only one sharp end is used. Changing the direction of the needle with one sharp end to 180 degree laparoscopically might be technically challenging.

Figure 7:
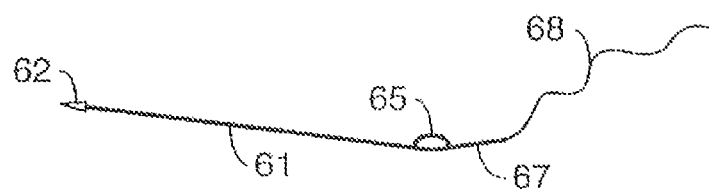
FIG. 7 is a lateral view of an exemplary angulated needle having a long segment with a pointed end on one side of the angle and a short segment having attached thread on the other side of the angle.

An alternative exemplary embodiment of a angulated needle is shown in FIG. 7. In this embodiment the angulated needle 60 has, for example, a long segment 61 with one sharp end 62 on one side of the angle 65. The needle 60 has a blunt short segment 67 on the other side of the angle 65. Thread 68 is attached to the end of the blunt short segment 67.

The angulated needle 60 allows penetration through the body wall as a straight needle. The needle 60 is inserted into and through the wall of the gallbladder. The needle is then flipped 180° and delivered back through the abdominal wall. The angulated needle 60 can be used to reposition a gall bladder or other structure during a laparoscopic procedure by, for example, puling or relaxing the suture, which eliminates or reduces the need for the insertion of one or more additional cannulas and laparoscopic instruments for that purpose. The angulation of the angulated needle 60 also reduces the chance of iatrogenic injury to surrounding structures by allowing the needle 60 to be flipped and then delivered back through the abdominal wall prior to contacting surrounding abdominal structures.

As illustrated in FIG. 9, a stand-alone laparoscopic medical instrument insertable through a laparoscopic trocar sleeve or cannula comprises an elongate shaft 80 formed of a plurality of a plurality of rigid cylindrical segments including a middle segment 82, three proximal end segments 84, 86, and 88, and three distal end segments 90, 92 and 94. During a laparoscopic procedure utilizing the instrument of FIG. 9, middle segment 82 transverses a laparoscopic cannula, trocar sleeve or instrument holder described herein, while proximal end segments 84, 86 and 88 are located outside the patient and distal end segments 90, 92, and 94 are located inside the patient. An operative tip 96 is disposed at one end of the shaft 80, more particularly at a free end of distal end segment 94, and actuator handles or grips 98 are disposed at an opposite end of the shaft, more particularly at a free end of proximal end segment 88. Actuator handles 98 are operatively connected to operative tip 96 via shaft 80 for controlling the operation of the tip.

Proximal end segments 84, 86 and 88 form a proximal shaft portion 100 that is independently bendable to form, for example, a C shaped configuration. Proximal end segments 84, 86, and 88 are connected to one another via joints or articulations 102 and 104 and to middle segment 82 via a joint or articulation 106.

Distal end segments 90, 92 and 94 form a distal shaft portion 108 that is independently bendable to form, for example, a C shaped configuration. Distal end segments 90, 92, and 94 are connected to one another via joints or articulations 110 and 112 and to middle segment 82 via a joint or articulation 114.

Operative tip 96 may be rotatable about a longitudinal axis 115. Further rotational capability may be provided by including a joint 116, 118, 120 along distal end segments 90, 92 or middle segment 82, where relative rotation of proximal and distal parts is effectuated about a longitudinal axis of the respective segment.

Proximal end portion 88 is provided with rotary actuators or knobs 122 for modifying the angles between adjacent distal end segments 90, 92, 94, for rotating operative tip 96 relative to distal end segment 94 about axis 114, and for implementing the longitudinal-axis rotation at joints 116, 118, and/or 120. Wing-nut-type clamps 124 may be provided at knobs 122 for releasably locking those actuators to maintain the angles between adjacent distal end segments 90, 92, 94, the rotary position of operative tip 96, and the longitudinal-axis rotation at joints 116, 118, and/or 120.

Clamping elements 126, 128, 130 may be provided at the articulations or joints 102, 104, 106 for locking the relative positions of middle segment 82, and proximal end segments 84, 86, 88. Alternatively, further knobs and wing-nut clamps (not shown) may be provided at the proximal end of the instrument for changing the angles between pairs of adjacent segments 82, 84, 86, 88.

During a laparoscopic surgical procedure, the axial position of the operative tip 96 may be adjusted by sliding the laparoscopic instrument of FIG. 9 into and out of the patient, for example, by modifying the position of the middle segment 82 relative to the respective cannula or instrument holder aperture. In addition, the axial position of operative tip 96 may be changed by adjusting the configuration of distal end portions 90, 92, 94 relative to one another. Strongly arced configurations have a shorter axial extent than configurations with more shallow arcs. Further degrees of freedom in the positioning of operative tip 96 relative to a surgical site are provided by the rotatability of operative tip 96 about the axis 114 and the rotatability at joints 116, 118, 120. The positional adjustability provided by articulations or joints 110, 112, 114 greatly enhances the practical capabilities of the instrument.

Figures 10, 11F:
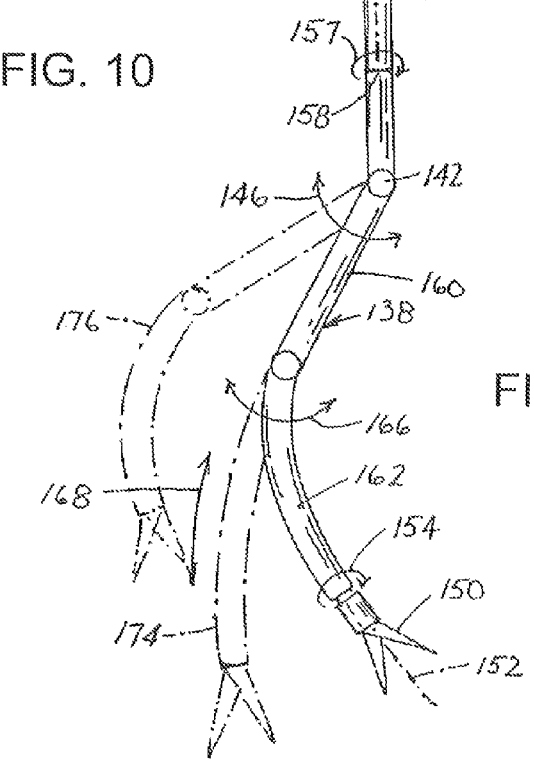
FIG. 10 is a schematic side elevational view of another laparoscopic instrument in accordance with the present invention.
FIGS. 11A-11F are diagrams of the instrument of FIG. 10, showing different possible operational configurations of the instrument.

FIG. 10 depicts another stand-alone laparoscopic medical instrument having a shaft 132 insertable through a laparoscopic trocar sleeve or cannula. Shaft 132 has a continuously flexible proximal end portion or segment 134, a rigid straight middle portion or segment 136, and a distal end portion 138. Proximal end portion 134 and distal end portion 136 are connected to opposite ends of middle portion 136 via respective articulations or joints 140 and 142, so that the proximal end portion and the distal end portion are laterally swingable relative to the middle portion, as indicated by dual headed arrows 144 and 146. Middle portion 136 constitutes about one-third of the total length of shaft 132.

Shaft 132 is provided at a proximal end, i.e., at the free end of proximal end portion 134, with a pair of hand grip actuators 144, and is further provided at a distal end, i.e., at the free end of distal end portion 138 with an operative tip 150 such as scissors, a forceps, a clamp, a cauterizing element, etc. Operative tip 150 is rotatable about a longitudinal axis 152 relative to the end of distal end portion 138, as indicated by a bidirectional arrow 154. As indicated by another bidirectional arrow 157, proximal end portion 134 and distal end portion 138 may be rotable relative to one another about a longitudinal instrument axis 156, owing to a ratable joint 158 exemplarily provided along middle portion 136.

Distal end portion 138 includes two segments or sections 160 and 162 pivotably connected to one another via an articulation or joint 164, as indicated by a dual headed arrow 166. Distal-most section 162 is continuously bendable along its length into an infinite number of smoothly curved generally C-shaped configurations, as indicated by an arrow 168. The more proximal section 160 may be rigid and linear or, alternatively, also continuously flexible along substantially its entire length and formable into a multitude of smoothly arced generally C-shaped configurations.

Proximal end portion 134 is provided along a linear proximal section (separately labeled) with a plurality of actuator knobs 170 and locking elements 172 for controllably modifying (a) the degree of curvature of proximal end portion 134 and distal end portion 138, particularly distal-most section 162, (b) the angles between portions 134 and 136 and portions 136 and 138, (c) the angle between sections 160 and 162, (d) the degree and direction of rotation of operative tip 150 about axis 152, and (e) the relative angular position of proximal end portion 134 and distal end portion 138, as determined by the operational status of joint 158. By way of illustration, a modified position and curvature of distal-most section 162 is indicated in FIG. 10 at 174. A modified position of proximal section 160 and a corresponding modified curvature of distal most section 162 are indicated in phantom at 176. An alternate position of proximal end portion 134 with respect to middle portion 136 is shown in phantom at 178.

FIGS. 11A-11F depict additional possible positional and curvature configurations of the instrument of FIG. 10, particularly distal end portion 138.

Figure 11A:
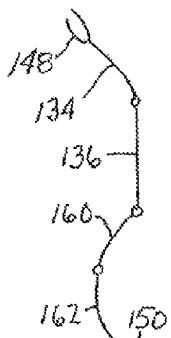
Figure 11B:
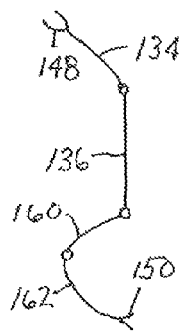
Figure 11C:
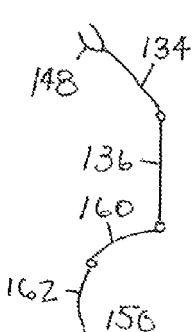
Figure 11D:
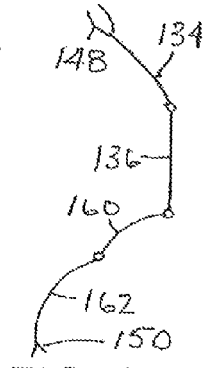
Figure 11E:
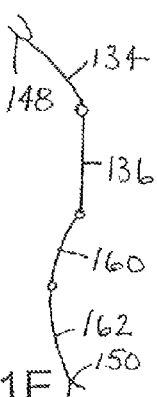

During a laparoscopic surgical procedure, the axial position of operative tip 150 may be adjusted by sliding the laparoscopic instrument of FIG. 10 into and out of the patient, for example, by modifying the position of middle portion 136 relative to the respective cannula or instrument holder aperture. In addition, the axial position of operative tip 150 may be changed by adjusting the configuration of distal end portion 138, as depicted in FIGS. 11A-11F. Strongly arced configurations (FIGS. 11B and 11C) have a shorter axial extent than configurations with more shallow arcs (FIGS. 11A, 11E). Further degrees of freedom in the positioning of operative tip 150 relative to a surgical site are provided by the rotatability of operative tip 150 about axis 152 and the rotatability at joint 158.

One or more of the actuator mechanisms including knobs 170 and locking elements 172 may be operatively connected to shaft 132 for bending distal section 162 (and optionally section 160) in a direction out of the plane of the drawing sheet.

Where proximal portion 134 of shaft 132 assumes a first C-shaped configuration in response to operation of a respective one of the knobs 170 and distal portion 138 (or 162) of the shaft assumes a second C-shaped configuration in response to operation of a second one of the knobs 170, the C-shaped configurations may face opposite sides of the shaft, thus forming shaft 132 into a generally S-shape.

As depicted in FIG. 12, a holder 180 for cannulas and laparoscopic surgical instruments such as those discussed above the reference to FIGS. 9-11F indicates a plate member 182 having a surrounding or perimetric edge 184 and a wall 186 surrounding the plate member. Wall 186 is provided with a plurality of anchoring elements such as eyelets 187 or hooks 189 for securing the holder 180 to a patient via suture thread.

Wall 186 is connected to a plate member 182 all along edge 184. Wall 186 has a longitudinal axis 188, with plate member 182 extending substantially transversely to that axis. Plate member 182 is provided with a plurality of separate and mutually spaced apertures or port members 190, 192 for receiving respective elongate laparoscopic instruments 194 and 196. Instrument 194 is configurable to have an S-shaped shaft 198 and may specifically take the form of the instruments discussed with reference to FIGS. 9 and 10-11F. Instrument 196 is a fiberoptic instrument including a camera 200 in the form of a charge coupled device and a bendable shaft 202. Shaft 202 has a proximal end portion 260 and a distal end portion 262 that may be independently flexed into continuous smooth C-shaped configurations as shown in the drawing. Alternatively, shaft 202 may be substantially identical to shaft 132 of the instrument shown in FIG. 10. The rotational capability discussed above with reference to operative tip 150 and joint 158 may be omitted from laparoscope 196. Laparoscope 196 has an operative tip 264 provided with the usual illumination aperture and imaging lens (neither shown). Actuators are omitted from the depiction in FIG. 12 of instruments 194 and 196 for purposes of simplicity. An actuator for controlling the operative tip 264 of laparoscope 196 may take the form of conventional controls for illumination and CCD operation, where a CCD is located at the operative tip of the device.

Holder 180 is an inflatable unit, both plate 182 and wall 186 being at least partially hollow for receiving a pressurizing fluid such as air. To that end, a tube 204 is connected to holder 180 for the delivery of air from a pressure source such as a syringe (not illustrated). A valve 206 is provided on tube 204. A second tube 208 with a valve 210 is connected to holder 180 for providing a channel for the conveyance of an insufflation gas such as carbon dioxide from a reservoir thereof (not shown) to the patient. An aperture 212 is provided along an inner surface 214 of wall 186 for enabling the delivery of the illustration gas to the patent via tube 208.

Wall 186 has a height dimension H1 at least as great as, and preferably substantially greater than, a height dimension H2 of plate member 182. Wall 186 has two end portions 216 and 218 extending as endless or annular flanges to plate member 182. Plate member 182 is located towards an upper end of wall 186, plate member 182 forming a shallow cup shape and a deep cup shape with flanges 216 and 218, respectively.

Wall 186 has inner diameters D1 and D2 of the free ends flanges 216 and 218, opposite plate member 182. These inner diameters D1 and D2 are larger than a diameter D3 of plate member 182, which is the inner diameter of wall 182 at the plate member. Consequently, cannula and instrument holder 180 has a flared or tapered profile on each side of plate 182. This flared or tapered shape may exhibit a curved or arced profile as shown in the drawing.

FIG. 13 is a cross-sectional view of holder 180 similar to FIG. 12, with laparoscopic instruments 194 and 196 removed to show possible valves 220 and 222 included in port members 190, 192. Valves 220 and 222 are not part of the present invention. Any known valve structure may be used in port members 190, 192.

It is possible for port members 190, 192 to be disposed entirely within plate member 182. In that case, the port members incorporate flat valves in the form of flexible, horizontally located membrane with openings for the passage of laparoscopic instruments.

As illustrated in FIG. 14, a flexible plate member 224 of a cannula and instrument holder 226 similar to that of FIGS. 12 and 13 has separate and mutually spaced apertures 3228 provided with rigid port membranes or cannulas 230 serving in part to elongate the apertures. Port members or cannulas 230 have a curvilinear or arced shape along their longitudinal dimensions and have flanges 232 and 234 that extend outside of plate member 224. Plate member 224 has a height H3 in a direction parallel to an axis of 236 of the cannula and instrument holder, which is at least as great as heights H4 and H5 of extension flanges 232.

Cannula and instrument holder 0226 has a side wall 237 that is substantially rigid in a region about plate member 224 and flexible at least in a distal flange region (inside the patient) spaced from plate member 224. Such a design facilitates cannula insertion in the abdominal wall opening and overall structural integrity of the system while under deforming external pressure (rigid part), and provides an improved degree of freedom, particularly in the lateral planes, within the system (flexible part).

Plate members 182 and 224, as well as walls 186 and 238 of holders 180 and 226 are flexible, but can acquire a semi-rigid form upon tilling with inflation fluid. The flexibility of the holders 180, 226 means that these devices can be rolled or folded into a compact deflated configuration for insertion into the umbilicus or other abdominal aperture. FIG. 15 shows such a compacted insertion configuration of an instrument holder 240 having port members 242. For assisting in the deployment of the instrument holder 240, tongs 244 may be used. Tongs 244 have a pair of handles 246 and a pair of substantially cylindrical jaw elements 248. The compacted instrument holder 240 is held between jaw elements 248 for insertion into the umbilicus. The compacted holder is held by a finger or instrument in place, while tongs 244 are opened slightly (arrow 247) and pulled (arrow 249) to separate jaw elements 248 from the holder 240. The holder 240 is then inflated in the umbilicus to the use configuration.

FIG. 16 depicts another instrument or cannula holder 250 for the insertion of multiple laparoscopic instruments into a patient through a single aperture in the abdominal wall of the patient. Instrument or cannula holder 250 includes a flared annular body member 252 provided at one end with a plurality of tapered or funnel-shaped introduction ports 254. Ports 254 include apertures 256 for the introduction of laparoscopic instruments as discussed hereinabove.

More particularly, the tapered or funnel-shaped port elements 254 each define a plurality of cross-sectional diameters D and each of said plurality of tapered funnel-shaped port elements 254 are connected to the flared annular body member 252 and extend proximally in a common direction therefrom, as indicated by the arrow 300. The taper of each of the tapered funnel-shaped port elements 254 decreases the plurality of cross-sectional diameters D in the proximal direction indicated by arrow 300.

The annular body member 252 has a C-shaped flared profile 302 along a longitudinal axis 304. The annular body member 252 defines a proximal aperture 306 and a perimeter 308. The plurality of tapered funnel-shaped port elements 254 each defines a distal aperture 310 and a perimeter 312. At least a portion 312' of the perimeter 312 of the plurality of tapered funnel-shaped port elements 254 is connected to the perimeter 308 of the proximal aperture 306 of the annular body member 252.

A remaining portion 314 of the perimeter 312 of at least two of the plurality of tapered funnel-shaped port elements 254 are connected to each other and intersect at a common point of intersection 316 generally coinciding with the center of the proximal aperture 306 of the annular body member 252. The distal apertures 310 defined by the two or more tapered funnel-shaped port elements 254 span the entire proximal aperture 306 defined by the annular body member 252.

The term "laparoscopic medical instrument" is used herein to denote all instruments utilizable in the performance of a laparoscopic medical procedure, including surgical instruments and laparoscopes.

While several exemplary embodiments of laparoscopic instruments and cannulas for the performance of laparoscopic procedures entirely through the umbilicus have been described herein, it is to be understood that variations may be made in the laparoscopic instruments and cannulas without departing from the spirit and scope of the present invention as defined by the appended claims.

The invention claimed is:

1. A method of laparoscopic surgery comprising the steps of:
grasping an inflatable instrument holder assembly having an insertion configuration for at least partial insertion of said holder assembly through an incision in a patient for at least partial insertion of said holder assembly into a patient cavity, and an in use configuration for use of said instrument holder assembly for access to said patient cavity, said instrument holder assembly radially compressed into a compact configuration for the insertion of said holder assembly at least partially through the incision in a patient, the radially compressed compacted instrument holder assembly defining an outer peripheral surface; and
inserting said radially compressed compacted instrument holder assembly at least partially through said incision,
wherein the step of grasping said radially compressed compacted inflatable instrument holder assembly is performed by retaining the outer peripheral surface of the radially compressed compacted instrument holder assembly via a pair of tongs.

2. The method of laparoscopic surgery as defined in claim 1, further comprising the step of:
inflating said compacted instrument holder assembly to the in use configuration for use of said instrument holder assembly for access to said patient cavity.

3. The method of laparoscopic surgery as defined in claim 1, wherein the step of grasping said inflatable instrument holder assembly that is performed by retaining the radially compressed compacted instrument holder assembly via a pair of tongs is performed via a pair of tongs that comprise:
a pair of handles pivotably joined to each other, the handles defining proximal and distal ends; and
a pair of jaw elements configured and disposed one on each of the distal ends of the handles to enable retention of said radially compressed compacted instrument holder assembly.

4. The method of laparoscopic surgery as defined in claim 3, further comprising the steps of:
holding the compacted instrument holder assembly in place in the incision; and
opening the pair of tongs slightly to enable movement of the jaw elements from the compacted instrument holder assembly.

5. The method of laparoscopic surgery as defined in claim 4, further comprising the steps of
pulling the pair of tongs in a direction proximal to a user; and
separating the pair of tongs from the compacted instrument holder assembly.

6. The method of laparoscopic surgery as defined in claim 5, further comprising the step of:
inflating said compacted instrument holder assembly, while positioned in the incision, to the in use configuration.

7. The method of laparoscopic surgery as defined in claim 3, wherein the step of retaining the radially compressed compacted instrument holder assembly via the pair of tongs is performed wherein the jaw elements are cylindrically shaped, the cylindrically shaped jaw elements grasping the radially compressed compacted instrument holder assembly therebetween.

* * * * *